United States Patent [19]

Rochard et al.

[11] Patent Number: 5,993,058
[45] Date of Patent: Nov. 30, 1999

[54] THERMOMECHANICAL CHARACTERIZATION SYSTEM USING A FAST INDUCTION HEATING DEVICE

[75] Inventors: Pierre Rochard, Orphin; Raymond Azzolini, St. Germain les Arpajon, both of France

[73] Assignee: Commissariat A L'Energie Atomique, Paris, France

[21] Appl. No.: 08/737,647

[22] PCT Filed: May 23, 1995

[86] PCT No.: PCT/FR95/00673

§ 371 Date: Nov. 21, 1996

§ 102(e) Date: Nov. 21, 1996

[87] PCT Pub. No.: WO95/33194

PCT Pub. Date: Dec. 7, 1995

[30] Foreign Application Priority Data

May 26, 1994 [FR] France .................................. 94 06388

[51] Int. Cl.⁶ .................................................. G01N 3/18
[52] U.S. Cl. .............................. 374/51; 374/46; 219/632; 219/634; 373/139
[58] Field of Search ........................ 374/51, 46; 219/632, 219/634, 637, 647; 373/139, 144, 145, 119; 73/818, 825

[56] References Cited

U.S. PATENT DOCUMENTS

| | | | |
|---|---|---|---|
| 1,756,457 | 4/1930 | Fourment | 219/634 |
| 1,995,811 | 3/1935 | Lon | 219/634 |
| 2,661,386 | 12/1953 | Lundgren | 373/144 |
| 3,636,293 | 1/1972 | Schneider et al. | 219/634 |
| 4,535,211 | 8/1985 | Carter | 219/632 |
| 4,608,473 | 8/1986 | Paek et al. | 373/139 |
| 4,687,343 | 8/1987 | Raffalski | 374/56 |
| 4,878,379 | 11/1989 | Deer | 374/46 |
| 5,260,538 | 11/1993 | Clary et al. | 219/634 |
| 5,308,947 | 5/1994 | Fleming, Jr. | 219/634 |
| 5,370,457 | 12/1994 | Iisuka | 374/51 |

FOREIGN PATENT DOCUMENTS

| | | | |
|---|---|---|---|
| 0430138 | 6/1991 | European Pat. Off. . | |
| 0567417 | 10/1993 | European Pat. Off. . | |
| 2204299 | 5/1974 | France | 374/51 |
| 2517920 | 6/1983 | France . | |
| 3047849 | 7/1982 | Germany . | |
| 406104076 | 4/1994 | Japan | 219/634 |
| 0291127 | 1/1971 | U.S.S.R. | 374/51 |
| 1432018 | 10/1988 | U.S.S.R. | 373/139 |
| 2195184 | 3/1988 | United Kingdom . | |
| 9308456 | 4/1993 | WIPO . | |

OTHER PUBLICATIONS

Allison; "Induction–Heated Reaction Vessels for the Chemical Industry"; Aug. 1964; pp. 210–214; AEI Engineering.

English abstract only of FR 2,399,391, published Apr. 6, 1979.

Beek, J.H., et al., "An environmental chamber for hertzian fracture testing," J. Phys. E. (GB), vol. 5, No. 7, pp. 710–712 (Jul. 1972).

*Primary Examiner*—Andrew Hirshfeld
*Attorney, Agent, or Firm*—Hayes Soloway Hennessey Grossman & Hage PC

[57] ABSTRACT

A system for thermomechanical characterization of material using an induction heating system capable of reaching a temperature of 3300° C. in not more than 20 seconds. This fast heating device comprises induction coils laid out at least partly around the sample (21) and generating induced currents, a susceptor placed between the sample and induction coils to transform induced currents into heat radiation, a thermal protection shield placed between the induction coils and susceptor shield to protect the induction coils from hear radiation emitted by the susceptor and an insulation material globally surrounding the induction coils. The invention has utility in fields using new materials, such as in the aeronautical and automotive industries.

10 Claims, 2 Drawing Sheets

THERMOMECHANICAL CHARACTERIZATION SYSTEM USING A FAST INDUCTION HEATING DEVICE

DESCRIPTION

1. Field of the Invention

The purpose of this invention is to develop a thermomechanical characterization system for a material sample subject to dynamic heating generated by an induction heating device.

It has many applications in aeronautical and automotive fields, and in all fields using new materials.

2. Background of the Invention

In order to characterize new materials, it is usually necessary to know their thermomechanical behavior, i.e. to be familiar with the deformation values of a material simultaneously subjected to dynamic heating and to a constraining force.

There are many conventional devices used to determine the thermomechanical properties of materials. However, most of these devices allow only a relatively slow temperature rise, which is not really representative of thermal stresses in a material in its "normal" usage.

Thus, different types of heating may be considered to enable a fast temperature rise:

heating by solar furnace as described in the Sep. 21–23 1992 International Symposium support document entitled "Ultra High Temperature Mechanical Testing" and particularly in the chapter entitled "Measurement of High Temperature Emissivity on Opaque Materials using a Temperature controlled solar furnace". This type of heating is capable of generating a thermal flux of about 6.4 $MW/cm^2$, which is capable of increasing the temperature of a sample to about 2800° C. However, use of this type of heating has the disadvantage that an integration sphere has to be used;

heating by $CO_2$ laser, as marketed by the OPTILAS Company. This heating system can provide a maximum power of 6 kW and therefore a maximum temperature of 2000° C. on the sample. This type of heating cannot increase the temperature quickly enough; furthermore, it cannot be used without an integration sphere;

heating by xenon arc lamps as marketed by the OPTILAS Company. This system is capable of generating sufficient power to bring the sample temperature up to 3300° C., but a large number of lamps have to be used at a very high price. Nevertheless, like the previous two types of heating by light radiation mentioned above, this type of heating is difficult to include in a thermomechanical characterization system;

heating by direct Joule effect which consists of passing an electrical current in a material sample. This type of heating is difficult to combine with a means used to generate mechanical forces, due to high thermal losses of these means and radiation losses from the sample surface;

resistor heating marketed by the IPSEN Company (in France) and the CENTORR Company (in U.S.A.). This system uses a graphite resistor and caulking screens made of graphite felt. This heating can bring the sample temperature up to 3000° C., but the rate of increase is slow at about 1500° C./h. Furthermore, this type of heating has the disadvantage that the resistor deteriorates with time by sublimation.

SUMMARY OF THE INVENTION

The purpose of this invention is to overcome the above-noted disadvantages. Consequently, it disposed a thermomechanical characterization system using an induction heating device capable of increasing the temperature of the sample up to 3300° C. in not more than 20 seconds.

This type of induction heating is achieved by a susceptor placed in a variable magnetic field which induces an electromotive force. Induced currents (or eddy currents) that pass through this susceptor are then transformed into heat. Therefore the sample is heated by radiation emitted by the susceptor.

More precisely, the invention relates to a thermomechanical characterization system for a material, comprising:

an insulating chamber inside which there is an approximately cylindrical shaped material sample;

fixed pressure means and mobile pressure means located at least partly in the chamber and between which the sample is positioned, these pressure means being capable of applying a compression force to the sample;

means of controlling the force to be applied to the sample;

sighting means to determine deformations experienced by the sample.

This system is characterized in that it comprises a fast induction heating means placed in the chamber and which comprises:

induction means placed at least partly around the sample and generating induced currents;

susceptor means placed between the sample and induction means to transform induced currents into heat radiation; and thermal protection means placed between said induction means and susceptor means to protect said induction means from heat radiation emitted by the susceptor means.

The induction means comprises at least one induction coil with a square cross-section and one side facing the thermal protection means and separated from the thermal protection means by an air gap 26. This coil may include an internal rib placed inside said coil to give a larger heat exchange area.

According to the invention, induction means comprise a refractory concrete layer that surrounds the induction coil on the sides that are not in contact with the thermal protection means.

According to one embodiment of the invention, the induction means comprise three induction coils parallel to each other.

According to one characteristic of the invention, the thermal protection means consist of an alumina ($Al_2O_3$) layer in which the pores are filled with a ceramic gel based coating.

The fast heating means also includes:

an upper plate covering the induction means, the susceptor means and the thermal protection means; and a lower plate laid out to be symmetric with the upper plate, with respect to the sample. At least part of these plates forms a duct through which a cooling liquid can circulate.

These heating means also comprise two upper and lower insulating plugs inserted between the upper plate and the pressure means, and between the lower plate and the pressure means respectively, to confine heat between the two plates.

The fast heating means according to the invention comprises radial perforations for the passage of a sighting means. The fast heating means can thus reach a temperature of at least 3300° C. at a rate of between approximately 160 and 200° C./sec.

DETAILED DESCRIPTION

Figure 1:
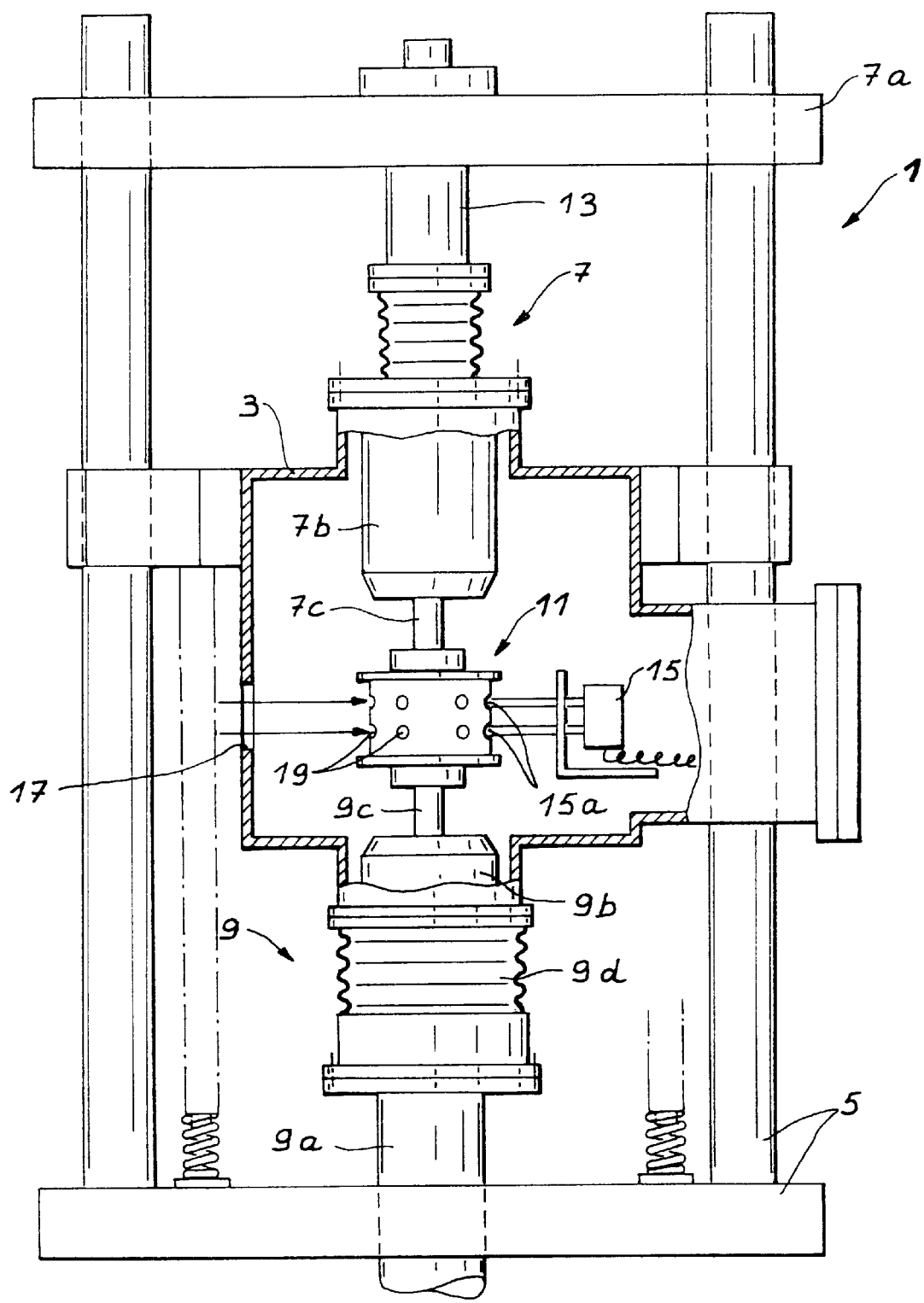
FIG. 1 shows a front partial sectional view of the material characterization system.

FIG. 1 shows a front view of the material thermomechanical characterization system 1. The insulating chamber 3 is shown in partial section in order to show the means located inside it.

This characterization system 1 comprises a mechanical test frame 5 to which fixed pressure means 7 and mobile pressure means 9 capable of compressing the sample are fixed, so that the sample is subjected to a mechanical compression force F. The sample is not shown in FIG. 1 since it is located inside the heating device 11.

Conventionally, the fixed pressure means 7 includes an upper cross-piece 7a, an upper hydraulic jaw 7b and a fixed piston 7c.

The mobile pressure means 9 conventionally includes a mobile actuator 9a, a lower hydraulic jaw 9b, a mobile piston 9c and a lower bellows 9d which moves actuator 9a.

The lower hydraulic jaws 9b and the upper hydraulic jaws 9c are placed at least partly inside the insulating chamber 3.

Mobile piston 9c and fixed piston 7c are also located inside the insulating chamber 3, and are even partly inserted inside the heating device 11.

The sample of material to be characterized is located inside the heating device 11, between the mobile piston 9c and the fixed piston 7c. Thus the sample may be heated simultaneously by the heating device 11 and compressed by pistons 7c and 9c.

A measurement cell 13 located in the upper part of the characterization system 1 measures the value of forces applied to the sample.

The sealed chamber 3 comprises openings 17, or drillings, through which the various sightings are made in order to make measurements on the sample:

there is a pyrometric sight for temperature control of the sample; and strain gauge sights used to measure deformations experienced by the sample up to a sample temperature of 250° C., using a laser strain gauge.

The sealed chamber 3 also comprises drillings 15a used to pass a contact strain gauge 15 used to measure deformations experienced by the sample if the sample temperature is less than 2500° C. These drillings 15a are plugged by Alumina plugs when the sample temperature is equal to or exceeds 2500° C.

Drillings 17 are also used to pass a thermocouple probe. This probe checks if the measured temperature of the sample corresponds to the stored set temperature values; it thus protects the heating device 11 against any abnormal temperature rise (particularly those that could be the result of an electrical flashover) and against any cooling defect.

Figure 2:
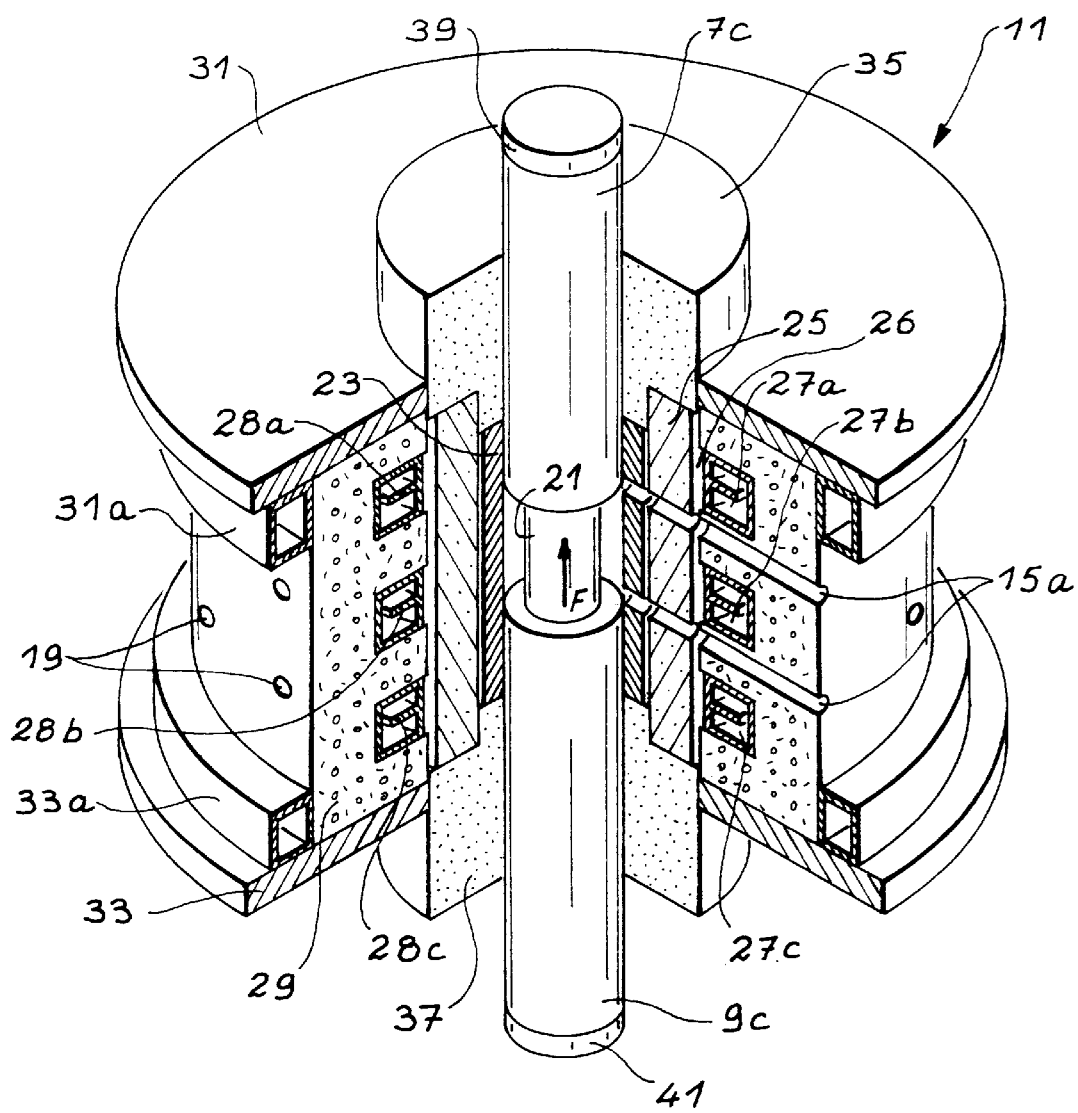
FIG. 2 shows a perspective view of the fast heating system according to the invention.

FIG. 2 shows a perspective view of the heating device 11. This figure shows a sectional view of the heating device 11. Sample 21 of the material to be studied is laid out between the fixed piston 7c and the mobile piston 9c. This sample 21 is subjected to a compression force F.

The following are located in circular layers around sample 21:

susceptor means 23, also more simply called susceptors;

thermal protection means 25, also called a thermal shield; and induction means 27a, 27b and 27c.

More precisely, these inductor means comprise at least one induction coil.

According to the preferred embodiment of the invention, inductor means comprise three induction coils 27a, 27b and 27c located parallel to each other in the longitudinal direction. These coils each have a square section; they each have one side which is separated from the thermal shield 25 by an air gap 26 so that they are not in direct contact with this thermal shield 25. They are surrounded on the other three sides by a layer of refractory concrete 29 providing insulation between the part of the device 11 subjected to high temperature and the chamber. This concrete layer 29 is very porous and is made of alumina ($Al_2O_3$), in which the pores are filled with a ceramic gel based coating. The assembly is capable of resisting a flashover voltage of about 3000 V, preventing diffusion of carbon inside the inductor.

It is preferable if these coils 27a, 27b and 27c each has an internal rib reference 28a, 28c and 28c respectively, in order to increase the coil exchange area, and consequently to facilitate elimination of heat generated by the coils towards the center of the heating device 11.

The susceptor 23 is placed approximately around sample 21 in the magnetic field created by induction coils 27a, 27b, 27c of the heating device 11. The currents induced by the coils (eddy currents) pass through this susceptor 23, and the susceptor transforms them into heat radiation. The temperature of the sample 21 to which this thermal radiation is applied increases up to the temperature chosen to study the material behavior. According to one embodiment of the invention, this susceptor is made of graphite.

The thermal shield 25 protects induction coils 27a, 27b, 27c from radiation emitted by susceptor 23. According to the invention, this thermal shield is made of insulating carbon.

The heating device 11 also includes disk-shaped plates, namely an upper plate 31 and a lower plate 33 which cover induction means 27a, 27b and 27c. These plates 31 and 33 are made of copper and each comprise a duct, 31a and 33a respectively, for the circulation of a cooling liquid in order to remove excess heat quickly. These plates also stiffen the entire device.

According to one embodiment of the invention, the upper 35 and lower 37 insulating plugs are housed in the central opening of plates 31 and 33 respectively. For example, these insulating plugs 35 and 37 may be made of rigid low density graphite felt, in order to confine heat inside the heating device 11. They also eliminate thermal gradients and radial and longitudinal heat losses.

According to one embodiment of the invention, heat confinement is further improved by placing thermal barriers 39 and 41 at the upper and lower ends of their pistons 7c and 9c respectively, minimizing longitudinal heat losses thus providing low longitudinal gradients on the sample.

FIG. 2 also shows drillings 19 for strain gauge or pyrometric sightings, and drillings 15a through which the contact strain gauge can pass.

Therefore the heating device 11 as shown in FIG. 2 is capable of generating a temperature of 3300° C. within a rise time of about 16 to 20 seconds, giving a temperature rise rate of about 160 to 200° C./sec. This type of performance can be achieved with a longitudinal temperature gradient on the sample of only 4% at 3200° C., and with a negligible radial temperature gradient on the sample.

Obviously, it will be understood that this heating device may also be used if slow heating is necessary, and if the required sample temperature is less than 3300° C.

We claim:

1. System for the thermomechanical characterization of a material, comprising:

an insulating chamber, inside which there is an approximately cylindrical sample of the material;

fixed pressure means and mobile pressure means located at least partly in the chamber and between which the sample is positioned, for applying a compression force (F) to the sample;

a measurement device connected to the chamber for measuring said force to be applied on the sample;

sighting means within the chamber to determine deformations experienced by the sample, fast induction heating means, placed in the chamber and comprising:

induction means placed at least partly around the sample for generating induced currents;

susceptor means placed between the sample and the induction means to transform the induced currents into heat radiation;

thermal protection means placed between the induction means and the susceptor induction means comprising at least one induction coil with a square cross-section and one side facing the thermal protection means, and separated from these thermal protection means by an air gap; and insulation means for providing a layer of material capable of resisting a high flashover voltage, said insulation means being located surrounding the induction means on the sides other than the side facing the thermal protection means, said material comprising a porous material in which the pores are filled with a ceramic gel based coating.

2. System according to claim 1, characterized in that the induction coil includes an internal rib housed inside said coil to provide a larger heat exchange area.

3. System according to claim 1, characterized in that the material layer consists of porous $Al_2O_3$ refractory concrete.

4. System according to claim 1, characterized in that the induction means comprise three induction coils parallel to each other.

5. System according to claim 1, characterized in that the thermal protection means consist of a carbon insulation thermal shield.

6. System according to claim 1, characterized in that the fast heating means also comprises:

an upper plate covering the induction means and insulation means; and a lower plate placed to be symmetric with the upper plate, with respect to the sample.

7. System according to claim 1, characterized in that the fast heating means include radial drillings in said fast heating means to enable said sighting means to pass through.

8. System according to claim 1, characterized in that the fast heating means can reach a temperature of at least 3300° C. at a rate of between approximately 160 and 200° C./sec.

9. System for the thermomechanical characterization of a material, comprising:

an insulating chamber, inside which there is an approximately cylindrical sample of the material;

fixed pressure means and mobile pressure means located at least partly in the chamber and between which the sample is positioned, for applying a compression force (F) to the sample;

a measurement device connected to the chamber for measuring said force to be applied on the sample;

sighting means within the chamber to determine deformations experienced by the sample, fast induction heating means, placed in the chamber and comprising:

induction means placed at least partly around the sample for generating induced currents;

susceptor means placed between the sample and the induction means to transform the induced currents into heat radiation;

thermal protection means placed between the induction means and the susceptor means, to protect said induction means from heat radiation emitted by the susceptor means, these induction means comprising at least one induction coil with a square cross-section and one side facing the thermal protection means, and separated from these thermal protection means by an air gap; and insulation means for providing a layer of material capable of resisting a high flashover voltage, said insulation means being located surrounding the induction means on the sides other than the side facing the thermal protection means, said fast induction heating means further including an upper plate covering the induction means and insulation means and a lower plate placed to be symmetric with the upper plate with respect to the sample and at least part of said plates form a duct to enable circulation of cooling liquid.

10. System for the thermomechanical characterization of a material, comprising:

an insulating chamber, inside which there is an approximately cylindrical sample of the material;

fixed pressure means and mobile pressure means located at least partly in the chamber and between which the sample is positioned, for applying a compression force (F) to the sample;

a measurement device connected to the chamber for measuring said force to be applied on the sample;

sighting means within the chamber to determine deformations experienced by the sample, fast induction heating means, placed in the chamber and comprising:

induction means placed at least partly around the sample for generating induced currents;

susceptor means placed between the sample and the induction means to transform the induced currents into heat radiation;

thermal protection means placed between the induction means and the susceptor means, to protect said induction means from heat radiation emitted by the susceptor means, these induction means comprising at least one induction coil with a square cross-section and one side facing the thermal protection means, and separated from these thermal protection means by an air gap; and insulation means for providing a layer of material capable of resisting a high flashover voltage, said insulation means being located surrounding the induction means on the sides other than the side facing the thermal protection means, said fast induction heating means further including an upper plate covering the induction means and insulation means and a lower plate placed to be symmetric with the upper plate with respect to the sample including an upper and a lower insulating plug inserted between said upper plate and the fixed pressure means and between the lower plate and said mobile pressure means, respectively, to confine heat between the two plates.

* * * * *

UNITED STATES PATENT AND TRADEMARK OFFICE
CERTIFICATE OF CORRECTION

PATENT NO.   : 5,993,058
DATED        : November 30, 1999
INVENTOR(S)  : Rochard et al.

It is certified that error appears in the above-identified patent and that said Letters Patent is hereby corrected as shown below:

Column 5,
Line 22, insert -- means, to protect said induction means from heat radiation emmited by the susceptor means, these -- after "susceptor"

Signed and Sealed this

Twelfth Day of February, 2002

*Attest:*

*Attesting Officer*

JAMES E. ROGAN
*Director of the United States Patent and Trademark Office*